United States Patent
Getman et al.

(10) Patent No.: US 6,711,942 B2
(45) Date of Patent: Mar. 30, 2004

(54) APPARATUS FOR DETERMINING AND/OR MONITORING THE VISCOSITY OF A MEDIUM IN A CONTAINER

(75) Inventors: Igor Getman, Lörrach (DE); Sergej Lopatin, Lörrach (DE)

(73) Assignee: Endress + Hauser GmbH & Co. KG (DE)

( * ) Notice: Subject to any disclaimer, the term of this patent is extended or adjusted under 35 U.S.C. 154(b) by 14 days.

(21) Appl. No.: 09/942,878

(22) Filed: Aug. 31, 2001

(65) Prior Publication Data

US 2002/0040592 A1 Apr. 11, 2002

Related U.S. Application Data

(60) Provisional application No. 60/264,006, filed on Jan. 26, 2001.

(30) Foreign Application Priority Data

Oct. 10, 2000 (DE) .......................... 100 50 299

(51) Int. Cl.[7] ............................................... G01N 11/10
(52) U.S. Cl. ..................... 73/54.25; 73/54.26; 73/54.27
(58) Field of Search .......................... 73/54.25, 54.24, 73/54.26, 54.27, 54.41, 290 V

(56) References Cited

U.S. PATENT DOCUMENTS

| 2,973,639 | A | * | 3/1961 | Banks ....................... 73/54.25 |
| 4,005,599 | A |   | 2/1977 | Schlatter et al. ........... 73/54.27 |
| 4,154,093 | A |   | 5/1979 | Smith et al. |
| 4,920,787 | A |   | 5/1990 | Dual et al. .................. 73/54.41 |
| 5,837,885 | A |   | 11/1998 | Goodbread et al. ........ 73/54.26 |
| 6,044,694 | A | * | 4/2000 | Anderson et al. .......... 73/54.25 |

FOREIGN PATENT DOCUMENTS

| CH | 637479 | 7/1983 |
| DE | 749077 | 6/1978 |
| DE | 4419684 | 12/1995 |
| GB | 2114745 | 8/1983 |
| WO | 14047 | 6/1994 |

* cited by examiner

Primary Examiner—Daniel S. Larkin
(74) Attorney, Agent, or Firm—Bacon & Thomas, PLLC

(57) ABSTRACT

The invention relates to an apparatus for determining and/or monitoring the viscosity of a medium in a container, having a unit which can oscillate, having a drive/reception unit and having a control/evaluation unit, in which case the unit which can oscillate is arranged at a defined measurement position within the container and/or in which case a unit which can oscillate is fitted such that it is immersed as far as a defined immersion depth in the medium, and in which case the drive/reception unit excites the unit which can oscillate to oscillate and/or in which case the drive/reception unit receives the oscillations from the unit which can oscillate. The control/evaluation unit uses the frequency/phase curve ($\phi=g(f)$) of the unit which can oscillate to determine the viscosity ($\eta$) of the medium.

15 Claims, 5 Drawing Sheets

APPARATUS FOR DETERMINING AND/OR MONITORING THE VISCOSITY OF A MEDIUM IN A CONTAINER

This application is based on Provisional Application No. 60/264,006, filed Jan. 26, 2001.

TECHNICAL FIELD

The invention relates to an apparatus for determining and/or monitoring the viscosity of a medium in a container, having a unit which can oscillate, having a drive/reception unit and having a control/evaluation unit, in which case the unit which can oscillate is arranged at a defined measurement position within the container and/or in which case a unit which can oscillate is fitted such that it is immersed as far as a defined immersion depth in the medium, and in which case the drive/reception unit excites the unit which can oscillate to oscillate and/or in which case the drive/reception unit receives the oscillations from the unit which can oscillate.

BACKGROUND OF THE INVENTION

Apparatuses are already known having at least one oscillating element, so-called vibration detectors, for detection and/or for monitoring the filling level of a medium in a container. The oscillating element is normally at least one oscillating rod, which is attached to a membrane. The membrane is stimulated to oscillate via an electromechanical transducer, for example a piezoelectric element. As a result of the oscillations of the membrane, the oscillating element which is attached to the membrane also oscillates. The "Liquiphant", which is produced and marketed by the applicant, should be mentioned at this point as a very well known example of a vibration detector.

Vibration detectors designed as filling level measurement devices use the effect that the oscillation frequency and the oscillation amplitude are dependent on the respective extent to which the oscillating element is covered: while the oscillating element can carry out its (resonant) oscillations freely and without damping in air, it experiences a frequency and amplitude change, that is to say a change in tuning, as soon as it is partially or completely immersed in the medium. In consequence, on the basis of a predetermined frequency change (the frequency is normally measured for filling level identification), a clear conclusion can be drawn on whether the filling level of the medium in the container has reached a predetermined point. Filling level measurement devices are normally used primarily to provide protection against overfilling or to provide protection against pumps running dry.

The damping of the oscillation of the oscillating element is also influenced by the density of the medium. Thus, if the coverage level is constant, there is a functional relationship between the frequency change and the density of the medium, so that vibration detectors are highly suitable for determining not only filling levels, but also densities.

In practice, in order to monitor and identify the filling level and/or the density of the medium in the container, the oscillations of the membrane are recorded and are converted by means of at least one piezoelectric element into electrical response signals. The electrical response signals are then evaluated by evaluation electronics. For filling level determination, the evaluation electronics monitor the oscillation frequency and/or the oscillation amplitude of the oscillating element and signal the state (sensor covered) or (sensor uncovered) as soon as the measurement values fall below or rise above a predetermined reference value. An appropriate indication to the operator can be produced visually and/or audibly. Alternatively or additionally, a switching process is initiated; thus, for example, an inlet or outlet valve on the container is opened or closed.

SUMMARY OF THE INVENTION

The invention is based on the object of using a vibration detector for determining and/or monitoring the viscosity of a medium in a container.

The object is achieved in that the control/evaluation unit uses the frequency/phase curve of the unit which can oscillate to determine the viscosity of the medium. The present invention is based on the fact that the damping of a unit which can oscillate is dependent on the viscosity of the medium with which it is in contact. As is known, the term viscosity means the internal friction of a liquid, which is caused by attraction forces between the molecules. The viscosity is largely dependent on the parameters pressure and temperature.

The frequency/phase curves of a unit which can oscillate, which curves have been recorded in media with different viscosities, differ considerably from one another—as can clearly be seen from the graphs illustrated in FIG. 1: the lower the medium viscosity, the steeper is the drop in the frequency/phase curve. It has been found to be particularly advantageous to determine the viscosity of the medium using the frequency change which occurs for two different phase values. A relative measurement is thus carried out in preference to an absolute measurement. As will be explained in more detail in the following text, either two phase values are set for this purpose with the associated frequency change being determined, or the system passes through a predetermined frequency band to find out when at least two predetermined phase values are reached. The frequencies corresponding to the phase values are in turn used to determine the frequency change and, from this, the viscosity of the medium.

In FIG. 2, the viscosity is plotted against the frequency change for various phase shifts. A logarithmic scale was chosen. The curves can be described by the following mathematical formula: $\log \eta = a \cdot \log \Delta f + b$, where a is virtually constant for all the curves, while the curves differ significantly in the constant b. In consequence, different phase shifts are reflected in a parallel shift in the frequency difference/viscosity curve along the frequency difference axis. The advantage of measuring the frequency change instead of the absolute frequency measurement is the increased measurement accuracy and—as will be described in detail in the following text—automatic elimination of disturbance variables, for example the density. The frequency change for a predetermined phase shift shows a clear dependency on the viscosity. In consequence, it is possible to determine the viscosity by determining the frequency difference for at least two predetermined phase values.

The influence of the density is visualized using the family of frequency/phase curves shown in FIG. 3 for a unit which can oscillate, in media with different densities: different densities lead to the frequency/phase curve being shifted parallel along the frequency axis. The higher the density, the lower is the oscillation frequency for the same phase value. The shape of the curves themselves is virtually identical in all cases. Since, according to the invention, relative values are measured rather than absolute values, the effect of changing density on the measurements is automatically eliminated.

According to a preferred development of the apparatus according to the invention, a piezo drive is used as the drive/reception unit. Piezo drives which can be used in conjunction with the present invention are known, for example, from EP 0 985 916 A1.

One advantageous development of the apparatus according to the invention provides for the drive unit to excite the unit which can oscillate to oscillate in a predetermined oscillation mode, in which case the oscillation mode is preferably the fundamental mode of the unit which can oscillate.

One preferred refinement of the apparatus according to the invention proposes that the control/evaluation unit have an associated memory unit in which data are stored which model the functional relationship between the frequency and the phase of the oscillations of the unit which can oscillate, for different damping conditions and for different viscosities. The data may be characteristics, formulae or measurement values.

The control/evaluation unit preferably sets at least two phase values which differ sufficiently from one another; after this, the control/evaluation unit determines the frequencies associated with the phase values and/or the corresponding frequency change in the oscillations of the unit which can oscillate, and determines the viscosity of the medium by comparing the frequency change which has already been found with the stored data.

According to one particularly advantageous refinement of the apparatus according to the invention, the at least two phase values are symmetrical with respect to the phase value φ=90°.

One advantageous embodiment of the apparatus according to the invention provides for the control/evaluation unit to select the range in which the frequencies which are used to determine the viscosity are located such that the functional relationship between the phase values and the frequencies is essentially linear.

According to one alternative embodiment of the apparatus according to the invention, the control/evaluation unit sets at least two frequencies which differ from one another; the phases between the transmitted signal and the response signal associated with the frequencies of the oscillations of the unit which can oscillate are then determined; in a final step, the control/evaluation unit determines the viscosity of the medium by comparing the determined phase values and the stored phase values.

According to one preferred variant of the last-mentioned alternative of the apparatus according to the invention, the control/evaluation unit has an associated signal generator which actuates the drive unit such that the unit which can oscillate oscillates successively at different oscillation frequencies, in which case the oscillation frequencies are within a selected frequency band (→ frequency sweep).

Furthermore, one development of the apparatus according to the invention allows the unit which can oscillate to be designed as a universal detector; the control/evaluation unit thus drives the unit which can oscillate as a limit switch in a first operating mode, and as a viscosity sensor in a second operating mode. The respective operating mode is predetermined by a program contained in the control/evaluation unit.

An input/output unit is preferably provided, via which adjustments can be made on the apparatus, or via which information is provided relating to the measurement values which the apparatus supplies. At least one bus line is provided for interchanging data between the unit which can oscillate and a remotely arranged monitoring point. The data interchange itself can be carried out by means of any desired transmission standard, for example Profibus PA, Fieldbus Foundation.

The invention will be explained in more detail with reference to the following drawings, in which:

DESCRIPTION OF THE PREFERRED EMBODIMENTS

Figure 1:
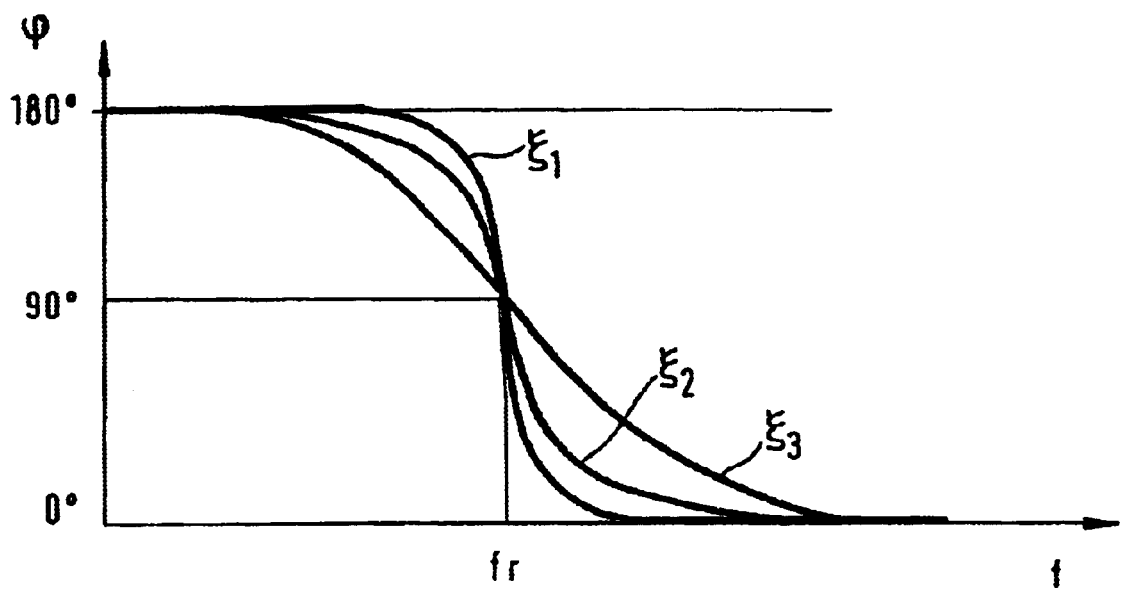
FIG. 1: shows a schematic illustration of the frequency/phase curves of the unit which can oscillate, for various damping coefficients.

FIG. 1 shows an illustration of three frequency/phase curves for a unit 2 which can oscillate, in media with various damping coefficients ξ. The inversion point of the three curves occurs at the resonant frequency fr, which is governed essentially by the stiffness of the membrane and by the mass of the oscillating element. As can be seen from FIG. 1, the phase φ between the drive signal and the response signal of the unit 2 which can oscillate is 90° at resonance. If the damping is low (damping coefficient ξ1) even minor frequency changes df lead to a sudden phase change of 180°— the phase change takes place abruptly. For larger damping coefficients ξ2, ξ3, the phase change from 0° to 180° takes place more or less smoothly. Within a certain frequency and phase range, the frequency/phase curves have a linear profile, with the gradient being dependent on the damping by the medium.

Figure 2:
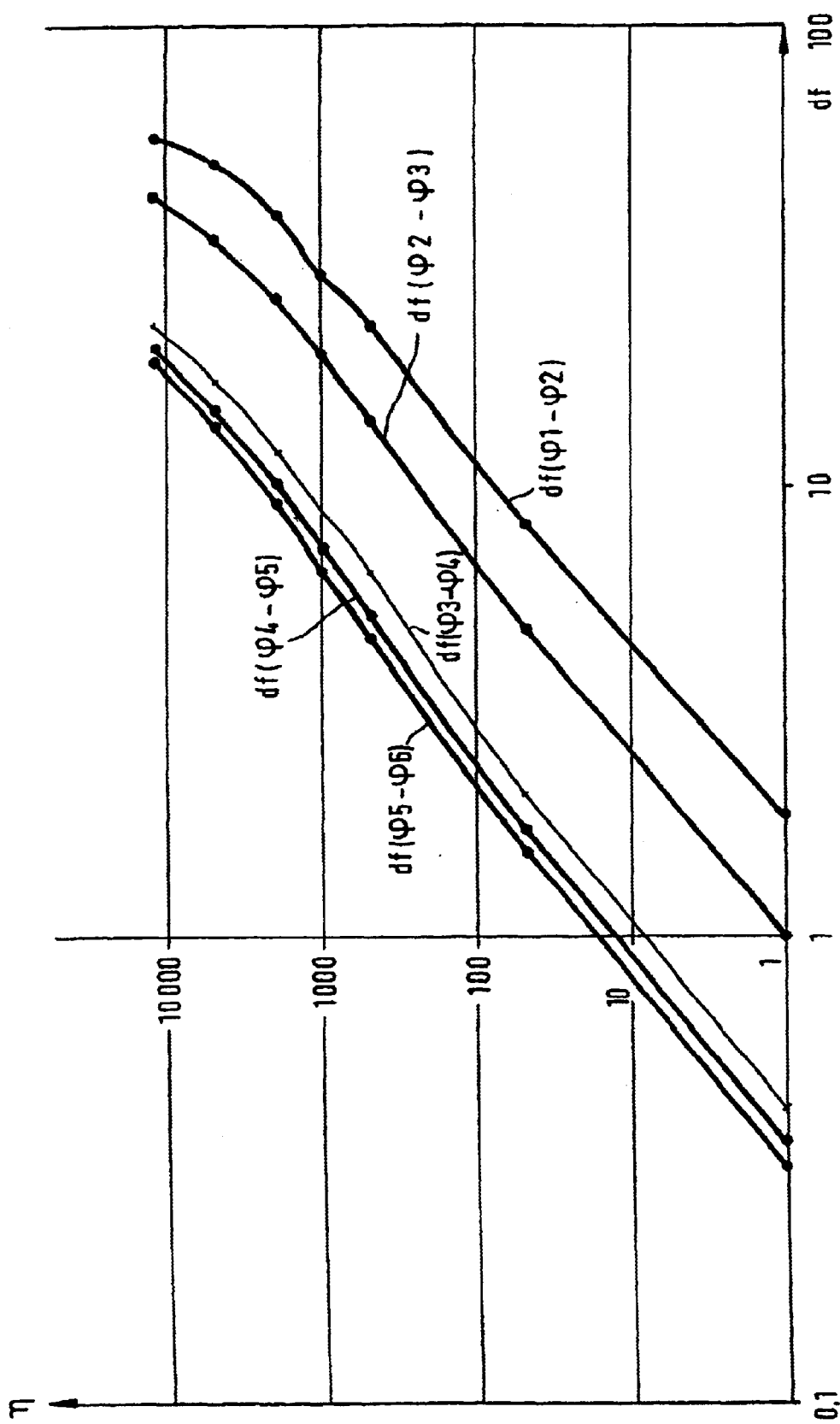
FIG. 2: shows a diagram showing the dependency of the viscosity on the frequency change, in the form of a graph.

FIG. 2 shows, schematically, the dependency of the viscosity η on the frequency difference df between the drive signal and the response signal, using a logarithmic scale. The family of curves represents the graphs for various phase shifts df(φn−φm) where n, m∈N, n≠m. The frequency change df for a predetermined phase shift df(φn−φm) indicates a clear dependency on the viscosity η. In consequence, it is possible to determine the viscosity η, according to a first alternative refinement of the apparatus 1 according to the invention, by measuring the phase difference df for at least two predetermined phase values φ1, φ2.

Figure 3:
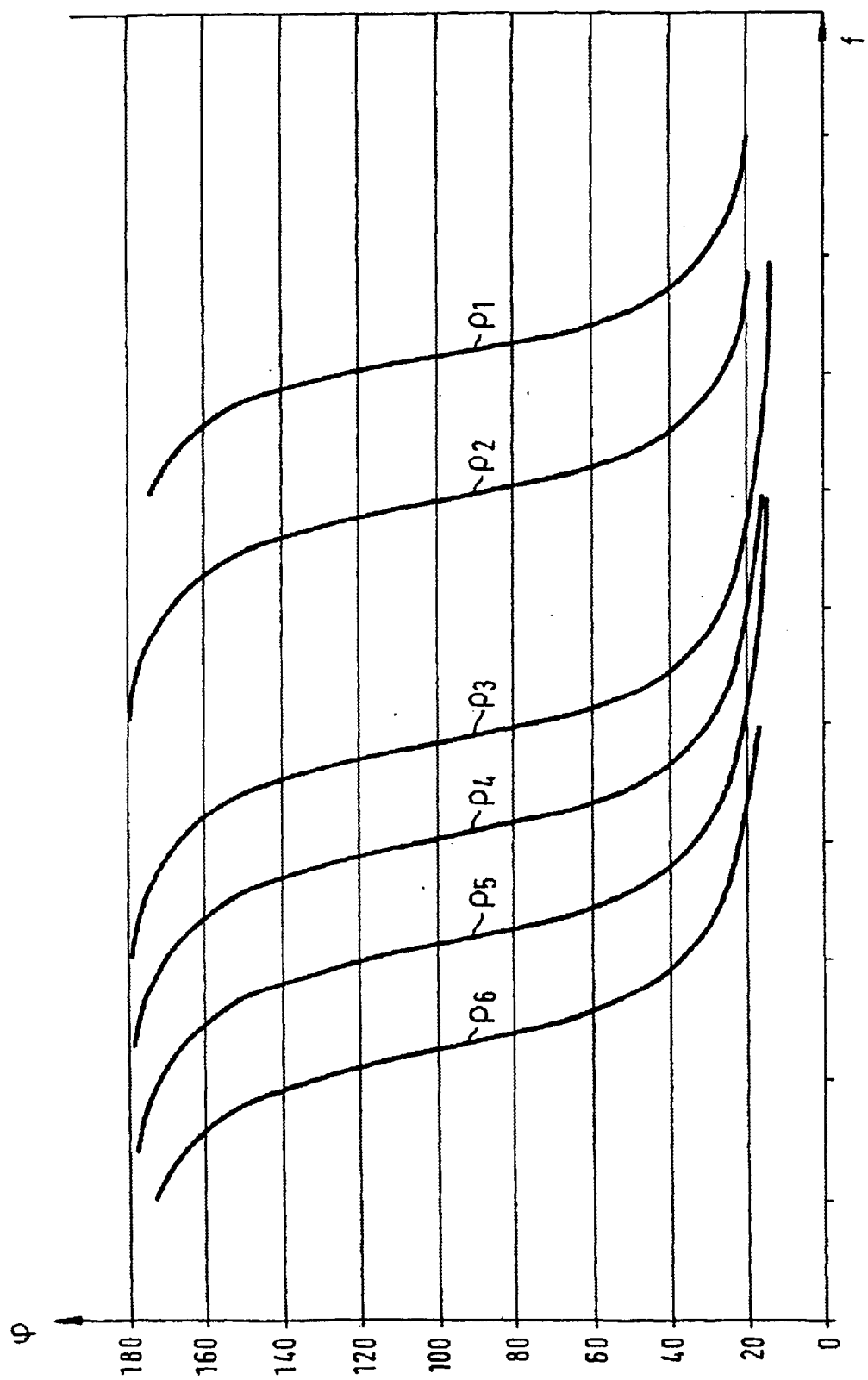
FIG. 3: shows a diagram which illustrates the frequency/phase curves for various media densities.

The influence of the density ρ is visualized on the basis of the frequency/phase curves, shown in FIG. 3, for a unit 2 which can oscillate, in media with different densities ρ: different densities ρ lead to the frequency/phase curve being shifted parallel along the frequency axis f. The greater the density ρ, the lower is the oscillation frequency for the same phase value φ. The shape of the curves themselves is virtually identical in all cases. Since, according to the invention, relative values (frequency changes or phase changes) are preferably used for evaluating the viscosity η rather than absolute values, the effect which the changing density ρ has on the measurement values is automatically eliminated.

Figure 4:
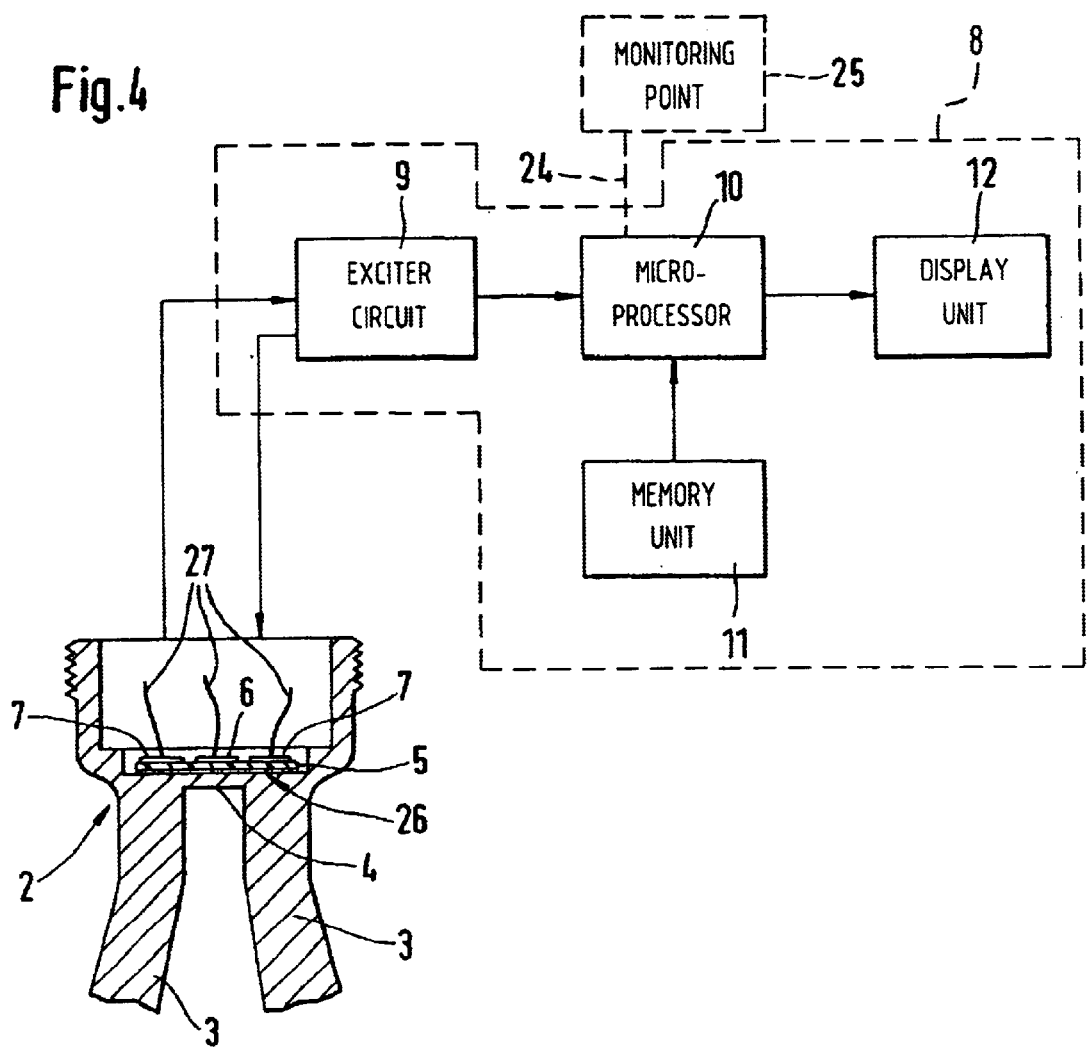
FIG. 4: shows a block diagram of a first embodiment of the apparatus according to the invention.

FIG. 4 shows a block diagram of a first embodiment of the apparatus 1 according to the invention. According to this first refinement, two predetermined phases φ1, φ2 are set successively between the drive signal and the response signal. The two phase values φ1, φ2 are set via the exciter circuit 9, which will be described in detail in the following text. The frequency values f1, f2 linked to the phase values φ1, φ2 are then determined. The frequency change df=f2−f1 is then used to determine the viscosity η of the medium, using the stored data. This first method for viscosity determination is very similar to the method using where a vibration detector can be used to determine that a predetermined filing level has been reached. The only difference in principle is that only the phase of the natural frequency or of the resonant frequency of the unit 2 which can oscillate is considered in the filling level measurement, while at least two phase values $\phi 1$, $\phi 2$ and the different frequencies f1, f2, and/or the corresponding frequency change di=f1-f2 of the unit 2 which can oscillate, are considered for the viscosity measurement. The exciter circuit 9, the micro-processor 10, the display unit 12 and the memory unit 11 form a control/evaluation unit 8 as shown in FIG. 4.

Owing to this high level of similarity, it is also relatively easy to design a unit 2 which can oscillate as a universal sensor for filling level, density, and/or viscosity measurement. As already mentioned, the filling level is normally determined by monitoring the resonant frequency fr. The viscosity η is preferably determined by setting two phase values $\phi 1$, $\phi 2$ which differ from one another and determining the corresponding frequencies, and/or the corresponding frequency change df=f1-f2. The frequency change df=f1-f2 for predetermined phase values $\phi 1$, $\phi 2$ is functionally dependent on the viscosity η.

The unit 2 which can oscillate is excited to oscillate via the piezoelectric exciter/reception unit which, in the illustrated case, comprises a piezoelectric element 5 in the form of a disk, a drive electrode 6, and two receiving electrodes 7. In this case, the piezoelectric element 5 carries out the function of an interface between the mechanical parts, that is to say the membrane 4 and the oscillating elements 3, and the electronic parts, that is to say the drive electrode 6 and the receiving electrode 7, of the unit 2 which can oscillate: firstly, the piezoelectric element 5 converts an electrical drive signal into mechanical oscillations; secondly, it converts mechanical oscillations into an electrical response signal. It is self-evident that a so-called stack drive can also be used instead of a piezoelectric element 5 in the form of a disk.

Figure 5:
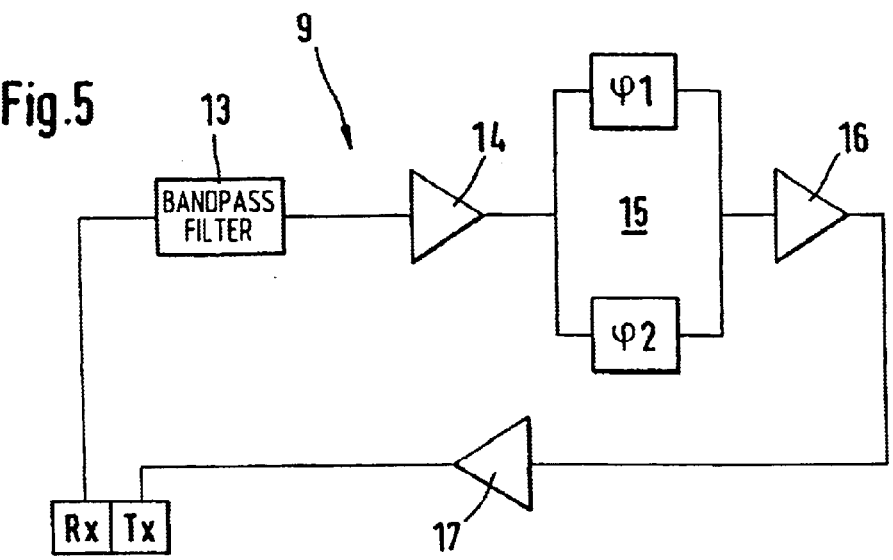
FIG. 5: shows a block diagram of the exciter circuit used in FIG. 4, FIG. 6: shows a graphical representation of a frequency/phase curve with visualization φ of a "frequency sweep" in two predetermined frequency bands.

FIG. 5 shows a block diagram of the exciter circuit 9 used in FIG. 4. As can be seen from the block diagram shown in FIG. 5, the exciter circuit 9 has a number of functions:it taps off the received signal Rx on the receiving electrodes 7. The response signal Rx is passed to the bandpass filter 13. The bandpass filter 13 preferably has a very narrow bandwidth, so that only the desired frequencies, or the desired frequency, are or is present at the output of the bandpass filter 13. The filtered response signal Rx is then supplied to the amplifier 14 and is amplified. In the illustrated case, two constant phase values $\phi 1$, $\phi 2$ are set in the phase shifter 15. The response signal is fed back to the drive electrode 6 as a drive signal Tx, via the amplifier 16 and the low-pass filter 17, and excites the unit 2 which can oscillate to oscillate with the respectively set phase value $\phi 1$, $\phi 2$.

The response signal Rx passes from the exciter circuit 9 to the microprocessor 10, which determines the corresponding frequency f1; f2 for each phase value $\phi 1$; $\phi 2$. The frequency change df=f2-f1 is then determined and is compared with corresponding data which are stored in the memory unit 11. The respective viscosity η of the medium can be determined from the clear functional relationship between the frequency change df and the viscosity η. The determined viscosity η of the medium may, for example, be indicated to the operator via the input/display unit 12. It is also possible, of course, to use the determined viscosity value to actuate control elements.

Figure 6:
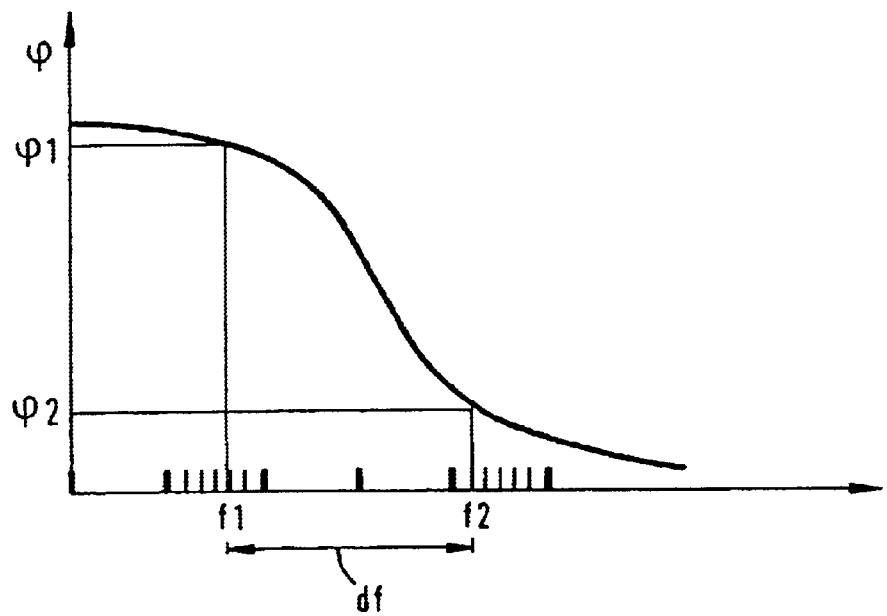
Figure 7:
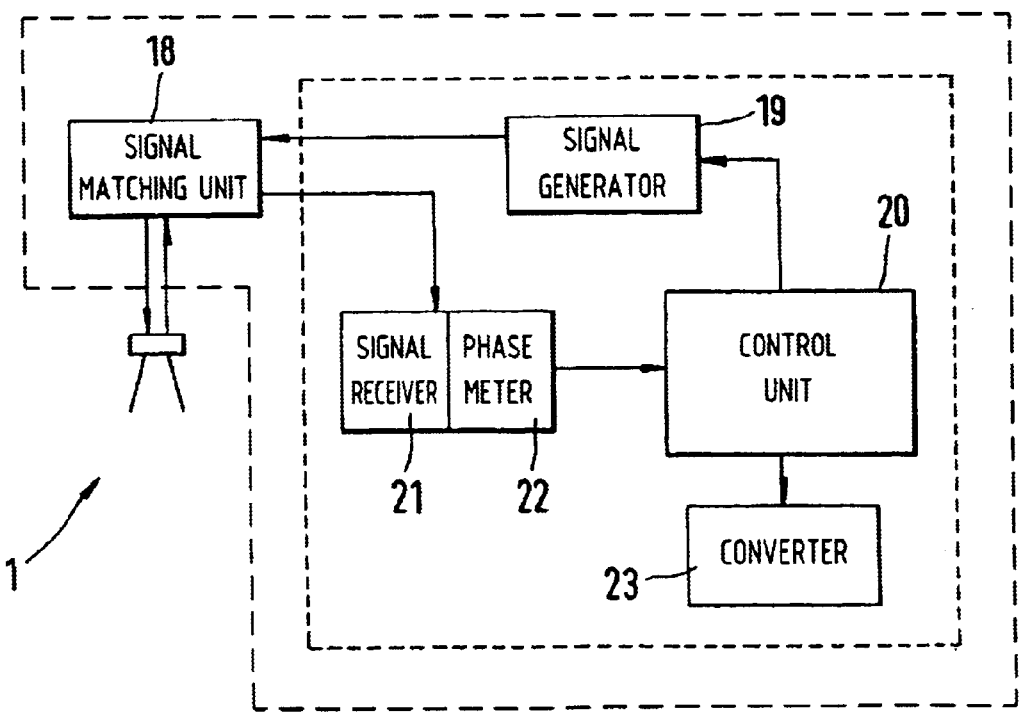
FIG. 7: shows a block diagram of a second embodiment of the apparatus according to the invention.

According to an alternative refinement of the apparatus 1 according to the invention, the frequency f is changed within predetermined frequency bands; the unit 2 which can oscillate is thus driven at different frequencies (→ frequency sweep). Different phase values are associated with the different frequencies. The continuous movement through certain frequency bands is shown graphically in FIG. 6. FIG. 7 shows a block diagram of this second embodiment of the apparatus 1 according to the invention.

In this second refinement of the apparatus according to the invention, two frequencies f1, f2, which are associated with two fixed, predetermined phase values $\phi 1$, $\phi 2$, are localized during the frequency sweep. Specifically, certain frequency ranges Δf1, Δf2 are swept through in continuous steps for this purpose. As soon as the fixed predetermined phase values $\phi 1$, $\phi 2$ are measured, the frequencies f1, f2 associated with the phase values $\phi 1$, $\phi 2$ are determined. The viscosity η of the medium is then determined from the frequency difference df=f2-f1.

The unit 2 which can oscillate is excited by a signal generator 19 with drive signals Tx at a predetermined frequency and preferably with a predetermined amplitude. The signal generator 19 is preferably a sine-wave generator. The signal generator 19 is preferably designed in such a way that both the frequency and the amplitude can be adjusted. The signal generator 19 receives the following input variables: the amplitude and possibly the offset, the start frequency and information about the output channel. The drive signals Tx are supplied to a signal matching unit 18, which preprocesses the signals in such a way that they can be read by the reception unit 21. The reception unit 21 thus receives the response signals Rx from the unit 2 which can oscillate. Its sampling rate must be designed such that no information is lost. A phase meter 22 in each case determines the corresponding phase shift between the drive signal and the response signal. The control unit 20 is responsible for the entire process for determining the frequency change df:it carries out the phase comparison, controls the frequency of the signal generator 19 and, finally, calculates the corresponding frequency change df. The viscosity η of the medium is then determined in the converter 23, using the determined frequency change df. Stored table values, characteristics, or formulae are used for this purpose.

In this embodiment, the signal switching unit 18, the signal generator 19, the control unit 20, the signal receiver 21, the phase meter 22 and the converter 23 form the control/evaluation unit 8 as shown in FIG. 7.

The bus line 24 refers to a common bus line as, for example, a Profibus® or Fieldbus Foundation™. The monitoring point 25 refers, for example, to a monitoring/evaluation unit as, for example, a computer, a SPS or whatever can be connected to a bus line. Reference electrode 26 refers to a ground electrode, and signal lines 27 refer to wires from the electrodes leading to the electronics.

The signal matching unit 18 contains, for example, the bandpass filter 13, low-pass filter 17 or amplifier 16 of FIG. 5 which are parts of the exciter circuit 9. Here, these electronics which are also part of the preprocessing of the response signals are combined in the signal matching unit 18. Hence, the signal matching unit 18 covers all further electronics to preprocess signals going to and coming from the unit 2.

LIST OF REFERENCE SYMBOLS

1. Apparatus according to the invention
2. Unit which can oscillate
3. Oscillating element
4. Membrane
5. Piezoelectric material
6. Exciter electrode
7. Receiver electrode
8. Control/evaluation unit
9. Exciter circuit
10. Microprocessor
11. Memory unit
12. Display unit
13. Bandpass filter
14. Amplifier 15. Phase shifter
16. Amplifier
17. Low-pass filter
18. Signal matching unit
19. Signal generator
20. Control unit
21. Signal receiver
22. Phase meter
23. Converter
24. Bus line
25. Monitoring point
26. Reference electrode
27. Signal line

What is claimed is:

1. An apparatus for determining and/or monitoring the level of a medium in a container and for determining and/or monitoring the viscosity of a medium in a container, having: a unit which can oscillate; an exciter/reception unit; and a control/evaluation unit, said unit is arranged at a defined measurement position within the container and/or in which case said unit is fitted such that it is immersed as far as a defined immersion depth in the medium in the container, and in which case, said exciter/reception unit excites said unit to oscillate and/or in which case said exciter/reception unit receives the oscillations from said unit, wherein:

said control/evaluation unit drives said unit as a limit switch in a first operating mode and as a viscosity sensor in a second operating mode;

said control/evaluation unit uses frequency (fr) changes to determine the level of the medium;

said control/evaluation unit uses the frequency/phase curve ($\phi=g(f)$) of said unit to determine the viscosity ($\eta$) of the medium; and said control/evaluation unit has an associated memory unit in which data are stored which model the functional relationship between the frequency (f) and the phase ($\phi$) of the oscillations of said unit which can oscillate, for different damping factors ($\xi$) and/or for different viscosities ($\eta$).

2. The apparatus as claimed in claim 1, wherein:
said exciter/reception unit excites said unit which can oscillate to oscillate in a predetermined oscillation mode, in which case the oscillation mode may be the fundamental mode of said unit.

3. The apparatus as claimed in claim 2, wherein:
said exciter/reception unit is a piezo drive which is in contact with a membrane to which at least one oscillating element is attached.

4. The apparatus as claimed in claim 1, wherein:
said exciter/reception unit is a piezo drive which is in contact with a membrane to which at least one oscillating element is attached.

5. The apparatus as claimed in claim 1 wherein:
said control/evaluation unit sets two phase values ($\phi 1, \phi 2$) which differ sufficiently from one another;
said control/evaluation unit determines the frequencies (f1, f2) associated with the phases ($\phi 1, \phi 2$) and/or determines the corresponding frequency change (df) in the oscillations of said unit; and
said control/evaluation unit determines the viscosity ($\eta$) of the medium by comparing the determined frequency change (df) with stored data.

6. The apparatus as claimed in claim 5, wherein:
the two phase values ($\phi 1, \phi 2$) are symmetrical with respect to the phase value $\phi=90°$.

7. The apparatus as claimed in claim 6, wherein:
said control/evaluation unit selects the range in which the frequencies (f) which are used to determine the viscosity ($\eta$) are located such that the functional relationship between the phase values ($\phi$) and the frequencies (f) is essentially linear.

8. The apparatus as claimed in claim 5, wherein:
said control/evaluation unit selects the range in which the frequencies (f) which are used to determine the viscosity ($\xi$) are located such that the functional relationship between the phase values ($\phi$) and the frequencies (f) is essentially linear.

9. The apparatus as claimed in claim 5, further comprising:
an input/output unit via which settings can be made on said apparatus or via which information is provided relating to the measurement values which said apparatus supplies.

10. The apparatus as claimed in claim 1, wherein:
said control/evaluation unit sets at least two different frequencies (f1, f2);
said control/evaluation unit determines the phase values ($\phi 1, \phi 2$) which are associated with the frequencies (f1, f2) of the oscillations of said unit which can oscillate, and
said control/evaluation unit determines the viscosity ($\eta$) of the medium by comparing the determined phase values ($\phi 1, \phi 2$) with stored data.

11. The apparatus as claimed in claim 10, wherein:
said control/evaluation unit has an associated signal generator, which actuates said exciter/reception unit such that said unit oscillates successively at different oscillation frequencies, in which case the oscillation frequencies are within at least one selected frequency band.

12. The apparatus as claimed in claim 9, further comprising:
an input/output unit via which settings can be made on said apparatus or via which information is provided relating to the measurement values which the apparatus supplies.

13. The apparatus as claimed in claim 10, further comprising:
an input/output unit via which settings can be made on said apparatus or via which information is provided relating to the measurement values which said apparatus supplies.

14. The apparatus as claimed in claim 1, further comprising:
an input/output unit via which settings can be made on said apparatus or via which information is provided relating to the measurement values which said apparatus supplies.

15. The apparatus as claimed in claim 1, further comprising:
a remotely arranged monitoring point; and
at least one bus line, via which said control/evaluation unit communicates with said remotely arranged monitoring point.

* * * * *